(12) United States Patent
Elvira et al.

(10) Patent No.: US 11,673,139 B2
(45) Date of Patent: Jun. 13, 2023

(54) MICROFLUIDIC PLATFORMS FOR DRUG DISCOVERY

(71) Applicant: UVic Industry Partnerships Inc., Victoria (CA)

(72) Inventors: Katherine S. Elvira, Victoria (CA); Elanna B. Stephenson, Victoria (CA); Jaime L. Korner, Victoria (CA)

( * ) Notice: Subject to any disclaimer, the term of this patent is extended or adjusted under 35 U.S.C. 154(b) by 231 days.

(21) Appl. No.: 17/163,164

(22) Filed: Jan. 29, 2021

(65) Prior Publication Data

US 2021/0237082 A1     Aug. 5, 2021

Related U.S. Application Data

(60) Provisional application No. 62/968,616, filed on Jan. 31, 2020.

(51) Int. Cl.
| | | |
|---|---|---|
| *C12N 15/10* | (2006.01) | |
| *B01L 3/00* | (2006.01) | |
| *B01L 7/00* | (2006.01) | |
| *F28F 3/12* | (2006.01) | |
| *G01N 33/15* | (2006.01) | |

(52) U.S. Cl.
CPC ........ *B01L 3/502792* (2013.01); *G01N 33/15* (2013.01); *B01L 2200/0673* (2013.01)

(58) Field of Classification Search
CPC ....... B01L 3/502792; B01L 2200/0673; B01L 9/527; B01L 2200/147; B01L 2300/0883; B01L 3/502784; G01N 33/15
See application file for complete search history.

(56) References Cited

U.S. PATENT DOCUMENTS

2019/0255529 A1 *   8/2019   Castell .................. A61K 9/107

* cited by examiner

*Primary Examiner* — Jennifer Wecker
*Assistant Examiner* — Oyeleye Alexander Alabi
(74) *Attorney, Agent, or Firm* — Klarquist Sparkman, LLP (57) ABSTRACT

A microfluidic device can include a plurality of channels defined in a substrate and a plurality of rails defined in a substrate. Each channel can comprise a respective channel inlet, a respective channel outlet, and one or more respective non-miscible fluid inlets fluidly coupled to the channel inlet. Each rail can comprise a rail inlet, and each channel outlet can be coupled to a respective rail inlet. One or more fluids introduced via the channel inlets can form first, second, and third droplets, respectively, and the plurality of rails can comprise first, second, and third rails configured such that droplets disposed on the rails form a tripartite droplet interface bilayer (DIB) network.

23 Claims, 9 Drawing Sheets

MICROFLUIDIC PLATFORMS FOR DRUG DISCOVERY

CROSS REFERENCE TO RELATED APPLICATION

This application claims the benefit of U.S. Provisional Application Ser. No. 62/968,616, entitled MICROFLUIDIC PLATFORMS FOR DRUG DISCOVERY, filed on Jan. 31, 2020, which is incorporated by reference herein.

BACKGROUND

In general, oral drug absorption is predicted using a variety of in vitro methods that range in complexity from cell-based assays to artificial membrane models. Drug absorption can occur through both carrier-mediated uptake and passive lipoidal diffusion. With cell-based techniques, the estimation of drug transport through both passive diffusion and carrier-mediated transport can be simultaneous, using supported monolayers of standard cell lines such as Caco-2 or Madin-Darby canine kidney (MDCK) to model transport out of the small intestine. Data gathered from these assays are used to calculate parameters such as apparent permeability coefficients ($P_{app}$) which correlates to in vivo fractional drug absorption (F). These cell lines are also able to mimic the physiological properties of enterocytes such as microvilli. Conversely, artificial cell membrane models, such as parallel artificial membrane permeability assays (PAMPA) and liposome-based assays, have other advantages: relatively low labor requirements, the ability to isolate the role of lipoidal diffusion, and tunability, which allows the mimicking of different types of membranes. However, there is no research to show that the membranes formed in PAMPA resemble true phospholipid bilayers as found in cells.

Accordingly, a need exists for improved artificial cell membrane models.

SUMMARY

The embodiments of microfluidic devices disclosed herein can be used to create pharmacokinetic compartment models configured to mimic or model the movement of pharmaceuticals through absorption, diffusion, or other methods within the human body. The compartment models can comprise a plurality of droplets, each configured to model a selected compartment of the human body. In particular embodiments, the compartment model can be configured to model the path of a drug proxy from the intestinal space into the blood via an enterocyte.

In a representative embodiment, a microfluidic device can comprise a plurality of channels defined in a substrate, each channel comprising a respective channel inlet, a respective channel outlet, and one or more respective non-miscible fluid inlets fluidly coupled to the channel inlet, and a plurality of rails defined in the substrate, each rail comprising a rail inlet, wherein each channel outlet is coupled to a respective rail inlet. One or more fluids introduced via the channel inlets can form first, second, and third droplets, respectively, and the plurality of rails can comprise first, second, and third rails configured to taper toward one another such that the first, second, and third droplets disposed on the rails contact one or more adjacent droplets to form a tripartite droplet interface bilayer (DIB) network.

In some embodiments, each channel inlet is coupled to a reservoir containing a respective fluid of the one or more fluids. One or more non-miscible fluid reservoirs can be coupled to the first, second, and third non-miscible fluid inlets. In some embodiments, each non-miscible fluid inlet can be coupled to a respective non-miscible fluid reservoir.

In some embodiments, the fluid reservoirs can be configured to contain oil (e.g., squalene) and the non-miscible fluid reservoirs can be configured to contain aqueous (e.g., buffer) respectively. In other embodiments, the fluid reservoirs can be configured to contain aqueous (e.g., buffer) and the non-miscible fluid reservoirs can be configured to contain oil (e.g., squalene) respectively. In some embodiments, the fluid reservoirs can be configured to contain aqueous (e.g., buffer) and the non-miscible fluid reservoir can be configured to contain a non-miscible aqueous phase (e.g., aqueous dextran) or vice versa.

The first droplet can be configured to mimic an entry point of a pharmaceutical agent into a subject to an area of pharmaceutical action. In other words, the first droplet can have a composition that corresponds to an area in a subject that absorbs a pharmaceutical agent. In some embodiments, there can be one to eight intermediate barriers between the entry point and the area of pharmaceutical action. In some embodiments, the first droplet can be configured to mimic an intestinal space of a subject, the second droplet is configured to mimic an intestinal cell cytosol of the subject, and the third droplet is configured to mimic the subject's blood. In other embodiments, the first droplet can be configured to mimic the subject's blood, the second droplet is configured to mimic endothelial cells, and the third droplet is configured to mimic the subject's brain.

In some embodiments, the microfluidic device can be a component in an assembly, comprising the microfluidic device and a heating platform configured to allow heating and viewing of the microfluidic device. The heating platform can comprise a base portion and a lid, and the microfluidic device can be disposed between the base and the lid.

Each pair of adjacent droplets can comprise a phospholipid bilayer between them. In some embodiments, each phospholipid bilayer comprises L-α-phosphatidylcholine (PC) and L-α-phosphatidylethanolamine (PE). In some embodiments, each phospholipid bilayer comprises polar brain lipid extract, total brain lipid extract, phosphatidylserine (PS), phosphatidylinositol (PI), cholesterol and/or sphingomyelin.

The substrate can comprise a first layer and a second layer. The plurality of channels can be disposed in the first layer, and the plurality of rails can be disposed in the second layer.

In some embodiments, at least one channel can comprise a meander such that the plurality of channels have equal lengths. In some embodiments, at least one non-miscible fluid inlet can comprise a meander such that all non-miscible fluid inlets have equal lengths. In some embodiments, at least one channel can comprise a meander sized to allow a droplet disposed within the at least one channel to equilibrate.

Ina representative embodiment, a method can comprise forming one or more DIB networks comprising at least first and second droplets, the first droplet comprising a pharmaceutical agent. The method can further comprise allowing the pharmaceutical agent to move from the first droplet into the second droplet, measuring a rate of movement of the pharmaceutical agent, and determining a diffusion model for the pharmaceutical agent based at least in part on the rate of movement. The first and second droplets can have different compositions and/or concentrations of pharmaceutical agent from one another.

In some embodiments, the DIB network can further comprise a third droplet, and the method can further comprise allowing the pharmaceutical agent to move from the second droplet into the third droplet. Measuring a rate of movement can comprise measuring a first rate of movement of the pharmaceutical agent from the first droplet to the second droplet, and measuring a second rate of movement of the pharmaceutical agent from the second droplet to the third droplet.

In some embodiments, forming the one or more DIB networks comprises disposing the first and second droplets into first and second channels, respectively, and flowing non-miscible fluid through first and second channels to carry the droplets. The first and second rails are configured to guide the droplets together to form a DIB network.

In another representative embodiment, an apparatus for forming DIB networks using microfluidic devices can comprise two or more droplet generators configured to generate droplets, an area configured to slow the speed of the droplets, an area configured to form DIB networks of a predetermined same and/or differing composition, and an area to stop the droplets for visualization.

The foregoing and other objects, features, and advantages of the disclosure will become more apparent from the following detailed description, which proceeds with reference to the accompanying figures.

DETAILED DESCRIPTION

Microfluidic devices such as those described below can be used to create pharmacokinetic compartment models using, for example, artificial cell membranes created from a phospholipid mixture designed to mimic human cells. Such compartment models, which can be referred to as droplet interface bilayer (DIB) networks, can be used to measure and predict pharmacologically relevant processes such as intestinal absorption. Such models can advantageously be used to help in drug development. Current methods of predicting passive drug transfer have limitations including biological dissimilarity, high time and labor input, and lack of control over the assay composition. The microfluidic devices described herein are configured to address these issues by allowing apparent permeability coefficients ($P_{app}$) to be calculated which correspond to in vivo fractional drug absorption (F). Further information regarding DIB network compartment models can be found in Elvira et al., (2020) A Bespoke Microfluidic Pharmacokinetic Compartment Model for Drug Absorption using Artificial Cell Membranes, *Lab on a Chip*, Volume 20, Issue 11, 1898-1906, which is incorporated by reference herein in its entirety.

The disclosed embodiments of a microfluidic device can be configured to create DIB networks that enable the prediction of pharmacologically relevant drug absorption using human-mimetic phospholipid compositions. The DIB networks created by these microfluidic devices can comprise cell-sized droplets formed in high-throughput with high reproducibility. In some embodiments, such DIB networks can be used to model the path of a drug proxy from the intestinal space into the blood via an enterocyte. Each droplet of the DIB network can be configured to model the pH and salt composition of its corresponding compartment in the human body.

Figure 1:
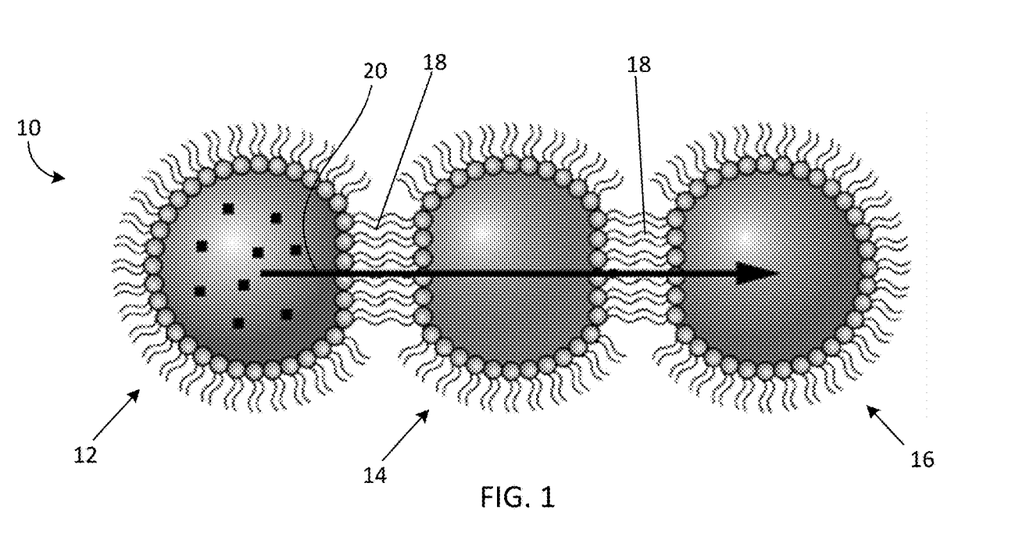
FIG. 1 illustrates an exemplary embodiment of a tripartite DIB network.

A DIB network can comprise a plurality of droplets configured to mimic human pharmacokinetics. FIG. 1 illustrates a representative tripartite DIB network 10 comprising a first droplet 12, a second droplet 14, and a third droplet 16. The first droplet 12 can mimic an entry point of a pharmaceutical agent into a subject to an area of pharmaceutical action (e.g., the blood). In other words, the first droplet can have a composition that corresponds to an area in a subject that absorbs a pharmaceutical agent. In some embodiments, the pharmaceutical agent can be disposed within the first droplet during formation of the first droplet. In other embodiments, the pharmaceutical agent can be disposed within one or more other droplets during formation of the droplets. In other embodiments, the pharmaceutical agent can be disposed outside the first droplet (e.g., in the non-miscible fluid) and can move from the outside of at least the first droplet to an interior space within at least the first droplet. In still other embodiments, the pharmaceutical agent can enter two or more droplets of the DIB network.

Each pair of adjacent droplets can comprise an intermediate barrier layer 18 between them. There can be, for example, between one and eight intermediate barriers 18 between the entry point and the area of pharmaceutical action. An intermediate barrier 18 can be, for example, a phospholipid bilayer formed by two adjacent droplets configured to mimic a cell membrane. A drug or other compound administered to the first droplet 12 can diffuse through the DIB network 10 as represented by arrow 20.

In some or all embodiments, the interior of each droplet represents a compartment (e.g., corresponding to a compartment of the human body), and the phospholipid bilayer between the droplets represents a cell membrane. In some particular embodiments, the first droplet 12 can be configured to mimic the intestinal space of a subject, the second droplet 14 can be configured to mimic an enterocyte of the subject (i.e., a cell of the subject's intestinal lining), and the third droplet 16 can be configured to mimic the subject's blood. In other embodiments, the first droplet can be configured to mimic the subject's blood, the second droplet is configured to mimic endothelial cells, and the third droplet is configured to mimic the subject's brain. In some embodiments, one or more droplets can be configured to mimic the same compartment.

Figure 2A:
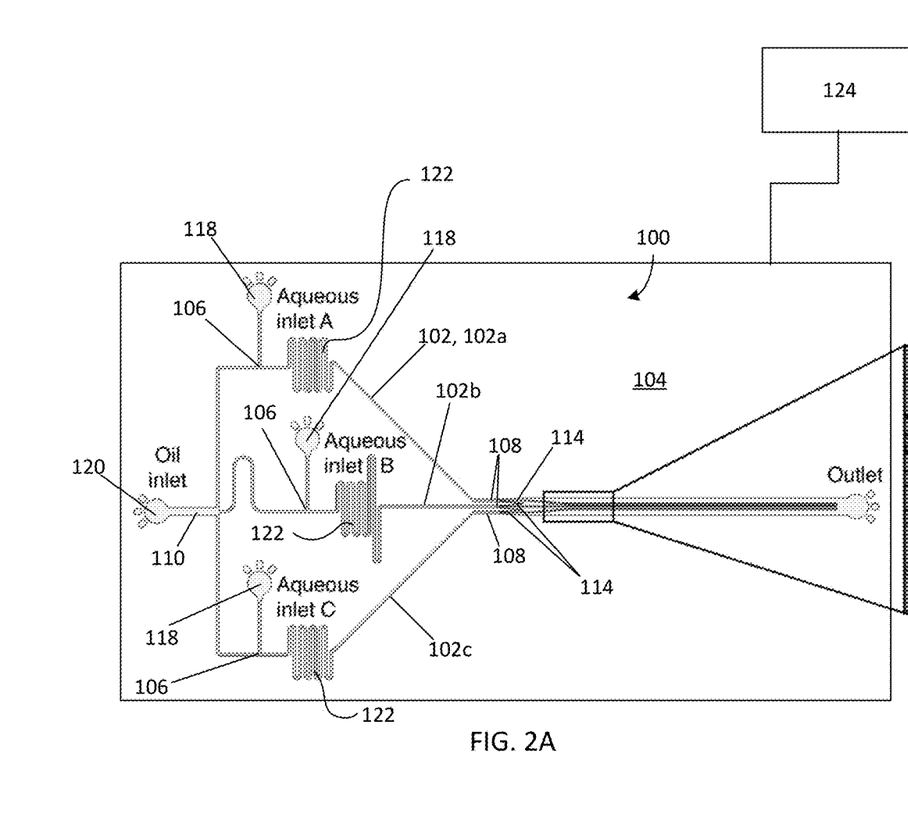
FIG. 2A illustrates an exemplary embodiment of a microfluidic device.
Figure 2B:
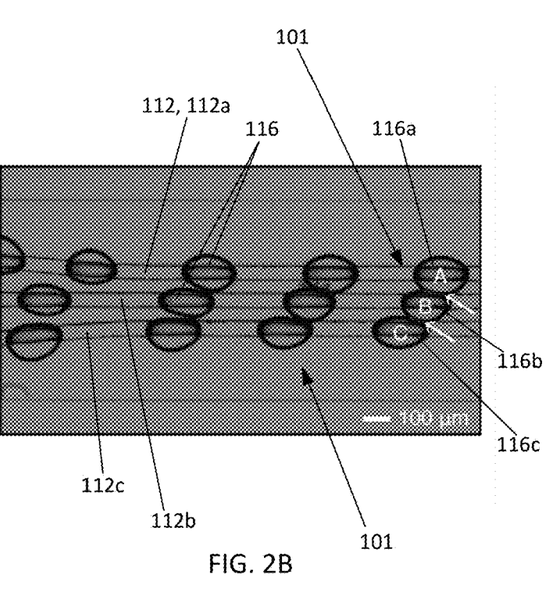
FIG. 2B illustrates a portion of the microfluidic device of FIG. 2A.

As mentioned, a microfluidic device can be used to create one or more tripartite DIB networks. Referring to FIGS. 2A-2B, in a representative embodiment, a microfluidic device 100 can be configured to create one or more DIB networks 101. The microfluidic device 100 can comprise one or more channels 102 (e.g., three channels 102a, 102b, and 102c) defined in a substrate 104. The substrate 104 can include a first layer and a second layer. The one or more channels 102 can be defined in the first layer, and one or more rails 112 can be defined in the second layer. In some embodiments, the first and second layers can fully overlap. In other embodiments, the first and second layers can at least partially overlap. In still other embodiments, the substrate 104 can comprise a single layer and the channels 102 and rails 112 can be defined in the single layer.

Figure 10:
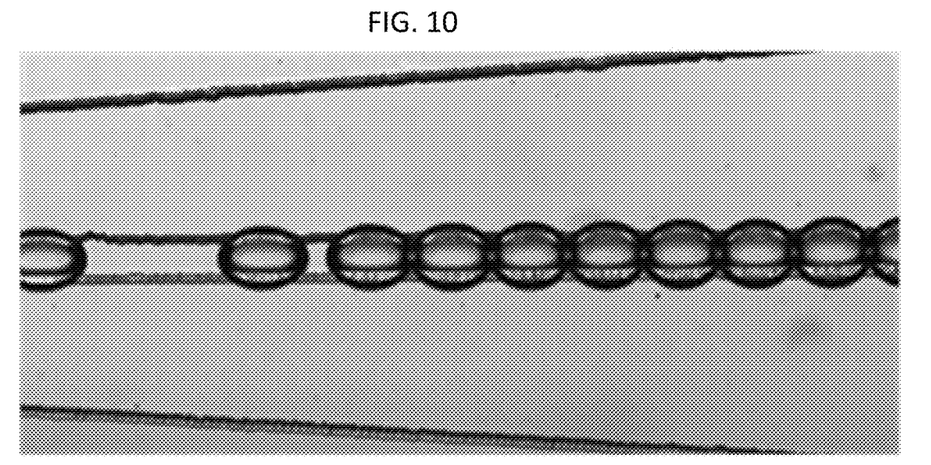
FIGS. 10-14 illustrate exemplary droplets formed from lipid solutions.

Each channel 102 can comprise a respective channel inlet 106, and a respective channel outlet 108. In the illustrated embodiment, each channel is coupled to a single non-miscible fluid inlet 110 at its respective channel inlet 106. However, in other embodiments, each channel 102 can be coupled to a respective non-miscible fluid inlet 110 via the channel inlet 106. As shown in FIG. 2B, which is an enlarged portion of FIG. 2A, the microfluidic device 100 can further comprise a plurality of rails 112 (e.g., three rails 112a, 112b, and 112c) defined in the substrate 104. Each rail 112 can comprise a rail inlet 114 and each rail inlet 114 can be coupled to a respective channel outlet 108. One or more fluids introduced via the channel inlets 106 can form droplets 116, for example, first, second, and third droplets 116a-116c, as shown in FIG. 2B. The plurality of rails 112 can comprise, for example, first, second, and third rails 112a-112c configured to guide the first, second, and third droplets 116a-116c together to form a tripartite DIB network. In some embodiments, at least a portion of each rail can be parallel to each adjacent rail. As shown in FIG. 2B, the DIB networks can be formed in parallel, that is, they can be formed from droplets disposed on adjacent rails. In other embodiments, they can be formed in sequence from droplets disposed on the same rail (e.g., as shown in FIG. 10).

Though the illustrated embodiment shows three channels 102 coupled to three rails 112, in other embodiments, the microfluidic device 100 can comprise any number of channels and/or rails in order to create DIB networks of various sizes (e.g., 2-part DIB networks, 4-part DIB networks, 5-part DIB networks, etc.). In such embodiments the DIB networks can also be formed in parallel (e.g., from droplets disposed on adjacent rails).

In some or all embodiments, each channel 102 can be coupled (e.g., at the channel inlet 106) to one or more fluid reservoirs 118 each containing a respective fluid. The fluid reservoirs 118 can be configured to generate a plurality of droplets 116 and each droplet can be configured to form a respective pharmacokinetic compartment in a DIB network.

Referring still to FIG. 2A, in some or all embodiments, each channel can be coupled to one or more non-miscible fluid reservoirs 120 (e.g., at the non-miscible fluid inlet). The non-miscible fluid reservoirs 120 can be configured to flow non-miscible fluid (e.g., oil such as squalene, or aqueous two-phase systems with dextran) into the channels 102. Droplets 116 disposed within the channels 102 can be carried through the channels 102 by the flow of non-miscible fluid. In some or all embodiments, multiple channels 102 can be coupled to a single non-miscible fluid reservoir 120. In other embodiments, each channel 102 can be coupled to one or more respective non-miscible fluid reservoirs 120. In some embodiments, each non-miscible fluid inlet 110 can form a T-junction with a respective channel inlet 106. In some embodiments, each non-miscible fluid inlet 110 can form other droplet generation geometries with a respective channel inlet 106.

In some embodiments, the fluid reservoirs can be configured to contain oil (e.g., squalene) and the non-miscible fluid reservoirs can be configured to contain aqueous (e.g., buffer) respectively. In other embodiments, the fluid reservoirs can be configured to contain aqueous (e.g., buffer) and the non-miscible fluid reservoirs can be configured to contain oil (e.g., squalene) respectively. In some embodiments, the fluid reservoirs can be configured to contain aqueous (e.g., buffer) and the non-miscible fluid reservoir can be configured to contain a non-miscible aqueous phase (e.g., aqueous dextran) or vice versa.

As shown in FIG. 2B, the plurality of channels 102 can taper toward each other, such that the channel outlets 108 can connect to respective rail inlets 114 of the plurality of rails 112. In the illustrated embodiment, for example, the microfluidic device can comprise first, second, and third channels 102a-102c coupled to first, second, and third rails 112a-112c, respectively. In other embodiments, the microfluidic device 100 can comprise a greater or fewer number of channels and rails.

First, second, and third droplets 116a-116c formed at the channel inlet 106 can travel along first, second, and third channels 102, respectively, to the first, second, and third rails 112. As best seen in FIG. 2B, the first, second, and third rails 112a, 112b, 112c can angle toward one another such that each of the first, second, and third droplets 116a-116c contacts at least one other adjacent droplet, allowing for barrier layer formation. The tapered angle of the rails 112 means that the droplets 116 are brought together at a slow speed, for example, about 40 $\mu ms^{-1}$. In a particular example, at their inlets, the rails can be 50 µm apart and can taper toward one another at, for example, a 5 degree angle. Bringing the droplets together at a slow speed advantageously promotes the formation of stable artificial cell membranes.

Each droplet can comprise a phospholipid monolayer such that a phospholipid bilayer can be formed between each pair of adjacent droplets. In some such embodiments, the phospholipid monolayer of each droplet can have a different composition such that the phospholipid bilayers formed between adjacent droplets are asymmetric. In other embodiments, each droplet can comprise its own phospholipid bilayer.

The phospholipid bilayer can comprise phospholipids associated with mammalian cells. In some embodiments, each phospholipid bilayer comprises L-α-phosphatidylcholine (PC) and L-α-phosphatidylethanolamine (PE). In some embodiments, each phospholipid bilayer comprises polar brain lipid extract, total brain lipid extract, phosphatidylserine (PS), phosphatidylinositol (PI), cholesterol and/or sphingomyelin. In some embodiments, each phospholipid bilayer can comprise additional molecules associated with mammalian cells, such as carbohydrates, glycolipids, and/or glycoproteins. In some embodiments, each phospholipid bilayer can comprise one or more membrane proteins. The membrane proteins may change the rate of movement of a pharmaceutical agent through the phospholipid bilayer.

In some or all embodiments, the substrate can comprise a first layer and a second layer. In such embodiments, the plurality of channels can be disposed in the first layer and the plurality of rails can be disposed in the second layer.

Figures 8A, 8B:
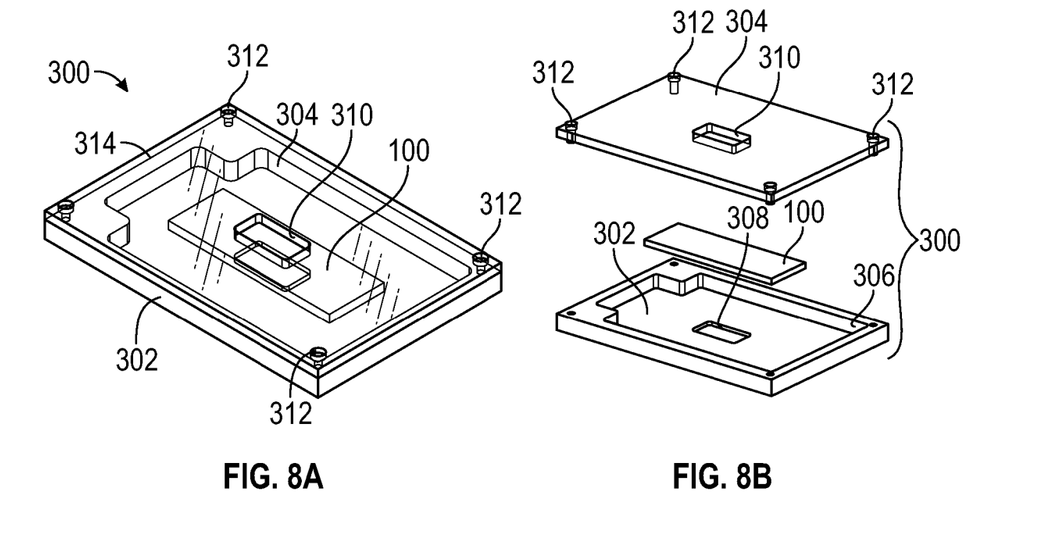
FIG. 8A illustrates a perspective view of an exemplary embodiment of a heating platform for heating a microfluidic device.
FIG. 8B illustrates an exploded view of the heating platform of FIG. 8A.

In some or all embodiments, the microfluidic device can be heated during use, using, for example, a heating platform. The heating platform can be configured to maintain the microfluidic device at a selected temperature, such as a physiological temperature of 37° C. The heating platform can be configured to fit into a microscope stage (e.g., a Nikon Ti2-E and/or Ti2-U inverted microscope). In some embodiments, the heating platform can comprise one or more resistive heaters and a proportional-integral-derivative (PID) controller 314 (FIG. 8A) to maintain programmed temperatures. FIGS. 8A-8B illustrate an exemplary heating platform 300 including a platform base 302 and a lid 304. A microfluidic device, such as device 100 described previously, can be disposed between the base 302 and the lid 304 in a recessed portion 306 defined in the base 302. The base 302 can define a first viewing aperture 308 configured to allow consistent heating and viewing of the microfluidic device 100 and the lid 304 can comprise a second viewing aperture 310. In some embodiments, the base 302 can comprise brass and the lid 304 can comprise acrylic (e.g., a clear acrylic). In some particular embodiments, the first and second viewing apertures 308, 310 can be 25.4 mm by 12.7 mm. The PID controller 314 can use a PID control system to maintain a setpoint temperature on the base. The base 302 can comprise one or more heating coils (e.g., 3 inch by 1 inch resistive heating foils that output 5W/sq. inch of heat). The heating foils can be coupled to a step down transformer which is connected to the output of a PID controller. A surface thermocouple can be used to monitor the temperature, and magnets 312 can be used to couple the lid 304 to the base 302. A method of calibrating the heating platform 300 is described in Example 4 below.

In some embodiments, the heating platform 300 and or/the microfluidic device 100 can be used to create DIB networks at different temperatures.

In some or all embodiments, at least one channel can comprise a meander such that the plurality of channels have equal lengths. In some or all embodiments, at least one non-miscible fluid inlet can comprise a meander such that all non-miscible fluid inlets have equal lengths. In some embodiments, the meanders can be configured to match propagation times between the droplets such that droplets disposed in adjacent rails eventually meet one another along the rails. As shown in FIG. 2A, in some or all embodiments, at least one channel 102 can comprise a meander 122 sized to allow a droplet 116 disposed within the at least one channel to equilibrate.

Referring still to FIGS. 2A-2B, the microfluidic device 100 can be used to create a tripartite DIB network 101 in the following exemplary manner. Non-miscible fluid (e.g., oil such as squalene) can be flowed from the non-miscible fluid reservoir 120 through the channels 102a-102c. A fluid can be flowed from each fluid reservoir 118 into a respective channel 102 such that droplets 116 are formed. Each droplet 116 can flow through a respective channel 102 and meander 122 such that the droplet can stabilize. The droplets 116 can then flow out of the channel outlets 108 and onto the rails 112. As the droplets 116 flow along the angled portion of the rails 112 they are guided into contact with one another to form a DIB network 101. Once the DIB network 101 has been formed, a pump (e.g., a pressure pump) can be used to stop the flow through the microfluidic device 100, thereby allowing assay quantification without the need for on-chip features such as pillars or electromagnetic valves. In other embodiments, standard on-chip features (e.g., standard features included in the microfluidic device) such as pillars or electromagnetic valves can be used to stop the movement of the DIB network.

Once the DIB network 101 has been created, passive diffusion of a pharmaceutical agent such as representative drug proxy (e.g. a fluorophore such as fluorescein) through the DIB network 101 can be measured using the method described in Example 2 below. The determined diffusion model and permeability coefficients ($P_{app}$) can then be used to predict the permeability coefficient of actual human tissue (e.g., intestinal tissue). The microfluidic assembly 100 can further comprise a controller 124 for controlling one or more components of the assay (e.g., imaging components, etc.), recording imaging data, generally controlling operation of the microfluidic device (e.g., heating elements, pumps, valves, etc.), and for displaying information gathered from the microfluidic assembly on a display unit.

Ina representative embodiment, a method can comprise forming one or more DIB networks comprising at least first and second droplets, the first droplet comprising a pharmaceutical agent, and allowing the pharmaceutical agent to move from the first droplet into the second droplet and vice versa. The method can further comprise measuring a rate of movement and determining a diffusion model based at least in part on the rate of movement. The first and second droplets can have different compositions from one another. In some cases, the rate of movement can be zero, meaning that there is no movement of the pharmaceutical agent.

In some or all embodiments, the DIB network can further comprise a third droplet, and the method can further comprise allowing the pharmaceutical agent to move from the second droplet into the third droplet. In such embodiments, measuring a rate of movement comprises measuring a first rate of movement from the first droplet to the second droplet, and measuring a second rate of movement from the second droplet to the third droplet.

In other embodiments, the DIB network can comprise any number of droplets. For example, the DIB network can comprise four, five, six, seven, eight, nine, or ten droplets. In such embodiments, measuring a rate of movement can including measuring the rate of movement between each pair of adjacent droplets and/or measuring the rate of movement between each pair of non-adjacent droplets.

In some or all embodiments, forming the one or more DIB networks can comprise disposing the first and second droplets into first and second channels, respectively, and flowing non-miscible fluid through first and second channels to carry the droplets into first and second rails. The first and second rails can be configured to guide the droplets together to form a DIB network.

In another representative embodiment, an apparatus for forming DIB networks using microfluidic devices can comprise two or more droplet generators configured to generate droplets, an area configured to slow the speed of the droplets, an area configured to form networks of droplets (e.g., two or more droplets) of a predetermined same and/or differing composition, and an area to stop the droplets for visualization. In some embodiments, the droplets can also have a predetermined size. In some or all embodiments, the area configured to slow the speed of the droplets can slow them to a speed of about 40 $\mu ms^{-1}$. In some or all embodiments, the area configured to slow the speed of the droplets can comprise one or more meanders. In some or all embodiments, the area configured to form networks of droplets can comprise one or more rails.

The microfluidic devices disclosed herein can predict pharmacokinetic properties of a drug including half-life, flux, and $P_{app}$. The disclosed devices advantageously demonstrate a greater degree of similar of $P_{app}$ to a true biological system (e.g., rat jujenum) than is possible with PAMPA. The microfluidic devices disclosed herein provide various advantages, for example, the rapid formation of multiple pharmacokinetic assays using only a pressure pump and one pressure channel per droplet type. The artificial cells (e.g., droplets) can advantageously be formed to sizes (e.g., 0.5 nL) and phospholipid compositions (e.g., PE and PC) that mimic human cells. The devices are capable of high-throughput analysis because the rate of DIB network formation allows for 900 or more assays to be performed per hour.

EXAMPLE 1

In a particular example, a microfluidic device, such as microfluidic device 100 described previously, can be used to create a tripartite DIB network, e.g. network 10 shown in FIG. 1, that mimics the path that an orally administered pharmaceutical or drug follows from the intestine to the blood.

The first droplet 12 can mimic the intestinal space, the second droplet 14 can mimic an enterocyte, and the third droplet 16 can mimic the blood. The interior of each droplet 12, 14, 16 comprises a buffer (see Table 1) that mimics the pH and salt composition of the respective compartment. The barrier layer or artificial membrane between each pair of adjacent droplets can be an equal mixture of the phospholipids L-α-phosphatidylcholine (PC) and L-α-phosphatidylethanolamine (PE). The size of the droplets 116 can mimic the volume of human cells.

TABLE 1

Composition of the buffers used for each pharmacokinetic compartment

| Droplet designation | Buffer | Salt |
| --- | --- | --- |
| Intestinal space | 10 mM Na$_2$HPO$_4$, pH 6.5 | 140 mM KCl |
| Enterocyte | 10 mM HEPES, pH 7.4 | 140 mM KCl |
| Blood | 10 mM Na$_2$CO$_3$, pH 7.4 | 140 mM NaCl |

The passive diffusion of a fluorophore, e.g., fluorescein, through the DIB network can be quantified to determine the rate of passive diffusion from the intestinal compartment to the blood compartment.

The microfluidic device comprises a substrate having two layers. The first layer contains the channels and geometries used for the formation of the three different types of droplets used to model each pharmacokinetic compartment. The second layer contains the rails, which are spaced 50 µm apart. The three rails encourage the three aqueous droplets, each comprising a phospholipid monolayer, to contact one another to form an artificial cell membrane between each pair of adjacent droplets. The 5 degree angle of the rails toward one another allows the droplets to be brought into contact at a slow speed of approximately 40 µms$^{-1}$.

To fabricate the microfluidic device, the first and second layers were printed onto acetate to create positive photomasks. A 50±2 µm thick layer of the negative photoresist SU-8 3050 was spincoated onto a silicon wafer and the edgebead was removed with a stream of acetone. The wafer was subjected to a soft bake (5 minutes at 35° C., 2 minutes at 65° C., and 30 minutes at 95° C.), and subsequently exposed to UV light (11.2 seconds, 19.96 mW/cm$^2$, OAI Model 800 mask aligner) through the first photomask. A second layer was spincoated, softbaked, aligned, and exposed to UV using the same parameters and the second layer photomask. Development removed the unexposed, noncrosslinked SU-8, and adhesion of the SU-8 features was accelerated by a final hard bake (30 min at 200° C.) and a third UV exposure (90 seconds, 19.96 mW/cm$^2$).

Trimethylchlorosilane (50 µL) and the wafer mold were placed under vacuum for 1 hour to ensure the deposition of a thin film of silane on the surface of the wafer. Polydimethylsiloxane (PDMS) base and curing agent were mixed together in a 10:1 ratio, poured over the aforementioned mold, degassed for 1 hour under vacuum to remove any air bubbles introduced during mixing, and cured overnight at 65° C. The cured PDMS was then peeled from the mold. Inlets and outlets for each device were punched using a 1 mm biopsy punch. To create the base of the device, a 10:1 mixture of PDMS base and curing agent was mixed, degassed and spincoated at 1200 rpm for 25 seconds onto the surface of glass microscope slides to create a thin layer. Both the PDMS devices and the coated glass slides were washed with soapy reverse osmosis (RO) water, rinsed with RO water, isopropyl alcohol, ethanol and Milli-Q water, blown dry with filtered air, baked at 90° C. for 30 minutes, treated with air plasma (e.g., using a Diener Electronic, Zepto ONE, for 37 seconds, at 29 W, 1.75 mbar) to activate the surfaces and placed into contact with each other to bond the surfaces together. The microfluidic devices were then stored at 65° C. for a minimum of 48 hours prior to use.

To prepare the lipid solutions, chloroform was removed from the lipid stock solutions by placing 10 mg (e.g., 400 µL of a 25 mgmL$^{-1}$ solution) of lipids in a 10 mL glass roundbottom flask, and rotating the flask under a stream of nitrogen gas to create a thin film. The flask was then placed in a desiccator under vacuum for 1 hour to remove residual solvent. For 1,2-diphytanoyl-sn-glycero-3-phosphocholine (DPhPC) solutions, 1 mL aqueous buffer (buffer composition is the same as that of the intestinal space in Table 1) was then added and the flask was vortexed to resuspend the lipids. After freezing and thawing 5 times using liquid nitrogen and warm water, the lipids were extruded 21 times through a 0.1 µm polycarbonate membrane (e.g., from Avanti Polar Lipids) at room temperature. For 1:1 PC:PE solutions, 1 mL of squalene was added to the flask, which was then vortexed for 30 s and stirred at 50° C. until the phospholipids dissolved. The final concentration was 5 mgmL$^{-1}$ PC and 5 mgmL$^{-1}$ PE in squalene. For absorption experiments, 100 M fluorescein sodium was added to the buffer.

During use, the microfluidic devices were mounted in a heating platform set to 37° C. on a microscope stage (e.g., a Nikon Eclipse Ti2-E or a Nikon Eclipse Ti2-U inverted microscope) for visualization. Brightfield images for statistical analysis were collected using a high-speed camera (e.g., a Motion Blitz EoSens Cube7 or a Phantom VEO 710L high-speed camera). Fluorescence and brightfield images for fluorescence experiments were captured using a measurement camera (e.g., a Hamamatsu ORCA Flash4.0 V3, with a Solis 1C cold white LED (e.g., from Thorlabs) and a GFP SemrockBrightline large field of view filter cube (e.g., from Nikon).

Reagents were introduced into the microfluidic devices using a pressure pump (e.g., an Elveflow OB1 MK3 pressure pump), four 1.5 mL Eppendorf tubes as reservoirs and four matched lengths of PTFE tubing. Squalene and aqueous buffers were introduced to the microfluidic device by applying a pressure of 100 mbar to 140 mbar to the squalene reservoir, and a pressure of 60 mbar to 100 mbar to each of the aqueous reservoirs. Following equilibration, the main chamber was monitored in Motion Blitz Director for quantification of device performance, and NIS Elements Advanced Research (Nikon, version 5.11.01) for fluorescence data collection. Following formation of a tripartite DIB network for a fluorescence experiment, flow was stopped from all reservoirs from within the Elveflow control software. Typical droplet speeds were approximately 450 µms$^{-1}$, allowing this full stop to be done without the use of triggers.

The speed at which droplets are brought into contact with each other impacts the formation of stable artificial cell membranes, and this is especially true when using phospholipids below their phase transition temperatures, as is the case herein. The disclosed microfluidic device embodiments advantageously use a pump having a fast response time, meaning that the flow can be stopped within 130 milliseconds of when a tripartite DIB network is formed and the assay begins.

EXAMPLE 2

An exemplary assay can proceed as follows to model the path an orally administered drug takes from the intestinal space, into enterocytes, and finally into the blood. Once the DIB network is formed and the flow is stopped within the microfluidic device, brightfield and fluorescence images were taken every 10 seconds with a 300 millisecond exposure time until experiment termination.

Figure 3A:
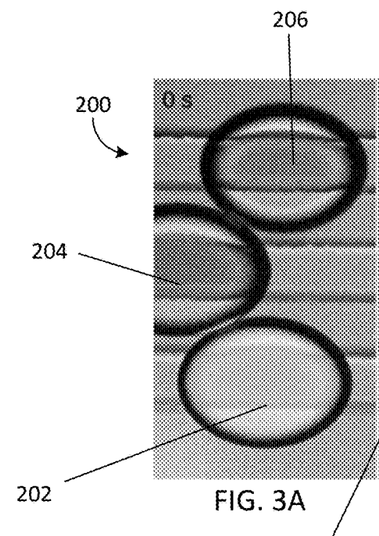
FIGS. 3A-3C illustrate movement of fluorophore through an exemplary tripartite DIB network.
Figures 3B, 3C:
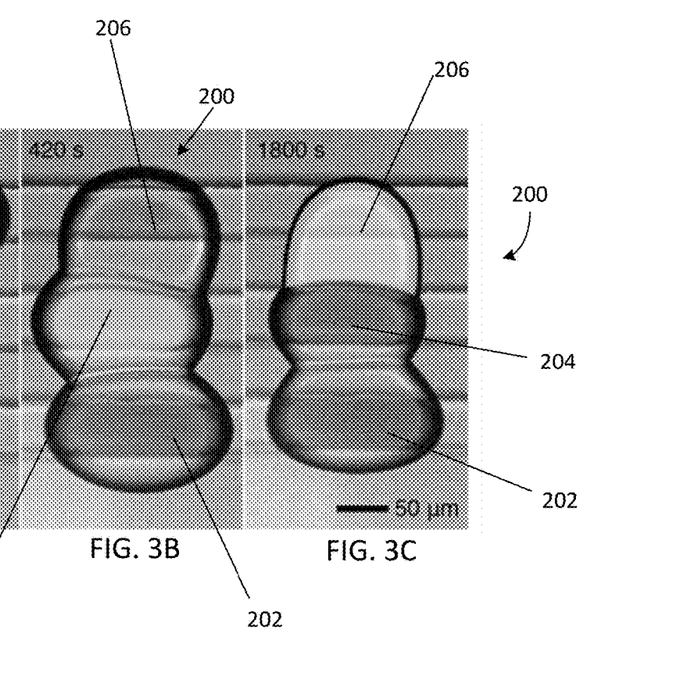
Figure 4:
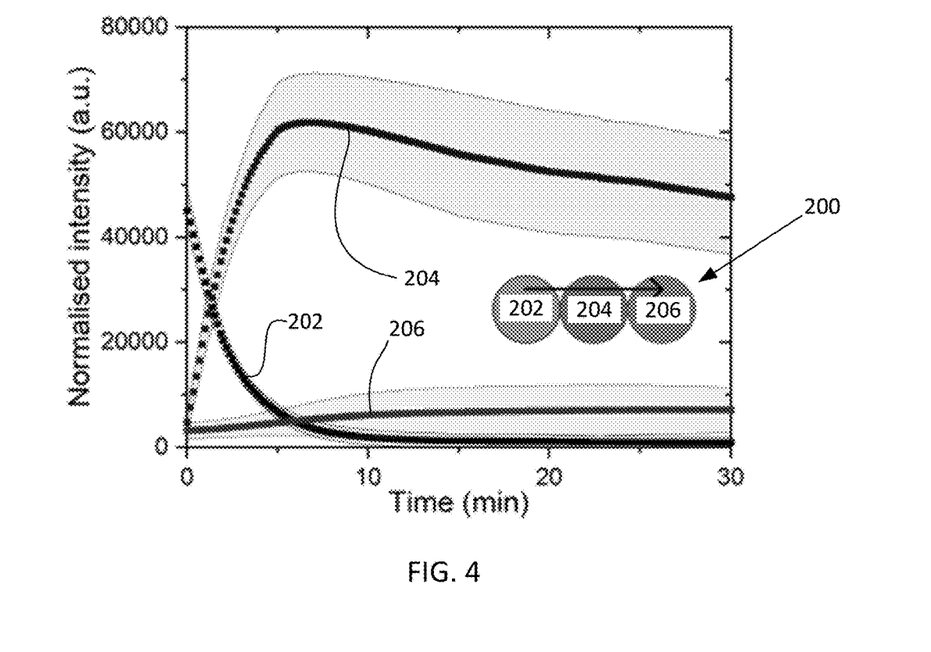
FIG. 4 is a graph of the change in fluorescence intensity over time for each compartment in the DIB network of FIGS. 3A-3C.

FIGS. 3A-3C show exemplary composite brightfield and fluorescence images of a DIB network 200 showing the diffusion of fluorophore from the first droplet 202 representing the intestinal compartment (FIG. 3A), to the second droplet 204 representing an enterocyte (FIG. 3B), to the third droplet 206 representing the blood compartment (FIG. 3C). Quantification of fluorescence intensity was performed via time-based measurement of mean intensity in regions of interest (ROIs) within each droplet in each frame using NIS Elements. Fluorescence intensity data was normalized for phospholipid bilayer surface area and droplet volume. To do this, bilayer diameters and droplet semi-axes were measured using, respectively, the "Distance Measurement" and the "Measurements and Annotations" modules in NIS Elements. Subsequent calculations were performed by approximating artificial cell membrane surface areas as ellipses and droplet volumes as ellipsoids. FIG. 4 shows the change in fluorescence intensity over time for each compartment 202, 204, 206 in the DIB network 200. The fluorophore is initially concentrated in the droplet 202 representing the intestinal compartment, but rapidly diffuses through the artificial cell membrane into the droplet 204 representing an enterocyte, and slowly diffuses through the artificial cell membrane into the droplet representing the blood. The intensity measurements were scaled based on changes in droplet volume over the course of the experiment, due to either evaporation or osmosis, using Equation (1).

$$I_s = I_t \frac{V_t}{V_0};$$ Equation (1)

where $I_s$ is the scaled intensity, $I_t$ is the intensity at time t, and $V_t$ and $V_0$ are the droplet volumes at times t and 0 respectively.

Figure 5:
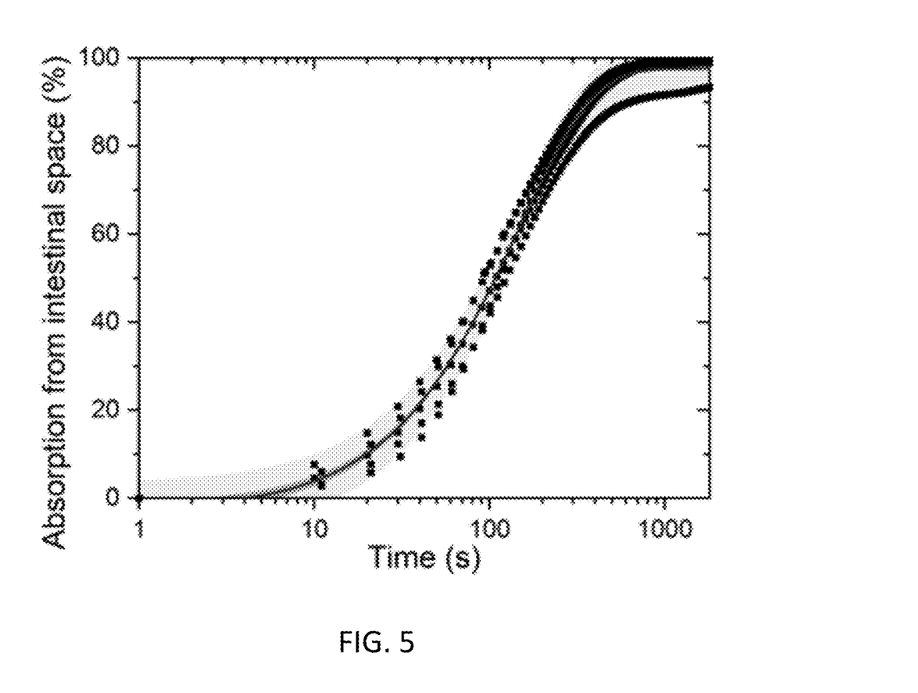
FIG. 5 is a graph of the absorption of fluorophore from the intestinal space compartment into the enterocyte compartment of the DIB network of FIGS. 3A-3C, shown as a percentage of fluorescence decrease from initial intensity.

FIG. 5 illustrates a graph of the absorption of the fluorophore from the intestinal space compartment 202 into the enterocyte compartment 204, shown as a percentage of fluorescence decrease from initial intensity. The rapid absorption of the fluorophore from the intestinal space can be clearly seen. To find the half-life ($t_{1/2}$) of the fluorophore in the intestinal space, an exponential curve can be fitted to the data. The slope of the intensity curve gives the diffusion rate. For example, in this instance $t_{1/2}=108\pm2$ seconds. The accuracy of this measurement was improved by accounting for the area dependence of the diffusion rates through the artificial cell membrane. The intensity flux was calculated using Equation (2).

$$j_t = \frac{\Delta I}{\Delta t} \frac{1}{A_{DIB,t}}$$ Equation (2)

where $j_t$ is the flux at time t, $\Delta I/\Delta t$ is the momentary slope, and $A_{DIB,t}$ is the measured artificial cell membrane area at time t.

Figure 6:
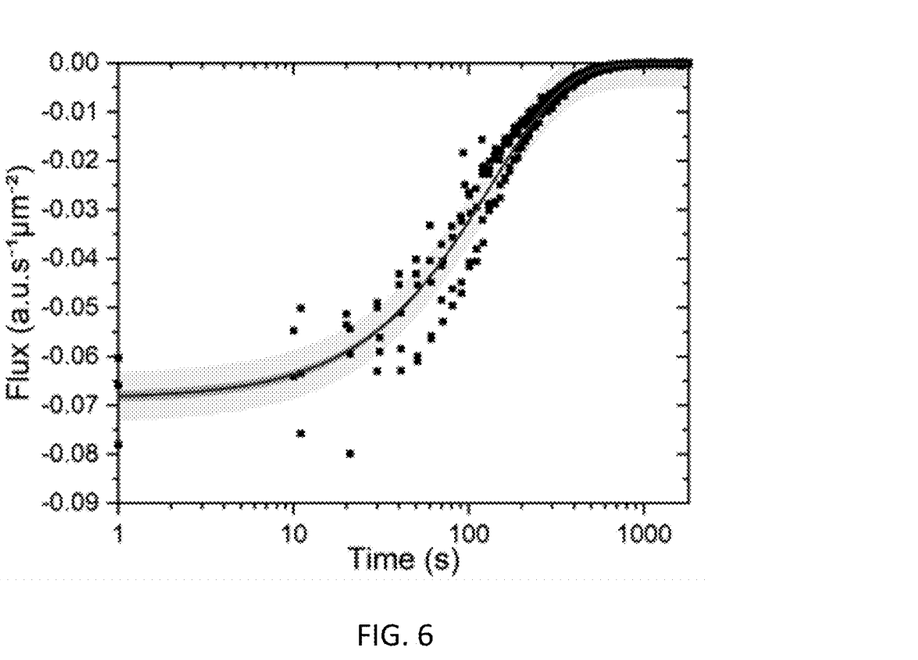
FIG. 6 is a graph of the flux of fluorophore from the intestinal compartment to the enterocyte compartment of the DIB network of FIGS. 3A-3C.

FIG. 6 illustrates a graph of the flux of fluorophore from the intestinal compartment 202 to the enterocyte 204, calculated using Equation (2). Maximum flux can be determined using the fitted curve, providing a measurement of the permeability of the membrane to the fluorophore. The $P_{app}$ of actual intestinal tissue can then be predicted using Equation (3). The DIB network was treated as a two compartment model, treating diffusion out of the intestinal space 202 as having the same magnitude as diffusion into the enterocyte 204.

$$P_{app} = \frac{-\Delta I_{max}}{\Delta t} \frac{V}{I_0 A}$$ Equation (3)

where $\Delta I/\Delta t$ (au/s) is the maximum rate of diffusion out of the first droplet 202, V (cm$^3$) is the initial volume of the second droplet 204, 10 (au) is the initial intensity of the first droplet 202, and A (cm$^2$) is the maximum artificial cell membrane surface area. $P_{app}$ was experimentally determined to be $(5.5\pm0.8)\times10^{-5}$ cms$^{-1}$ from the data shown in FIG. 6. In some embodiments, intensity can be converted to concentration through use of calibration curves.

Figure 7A:
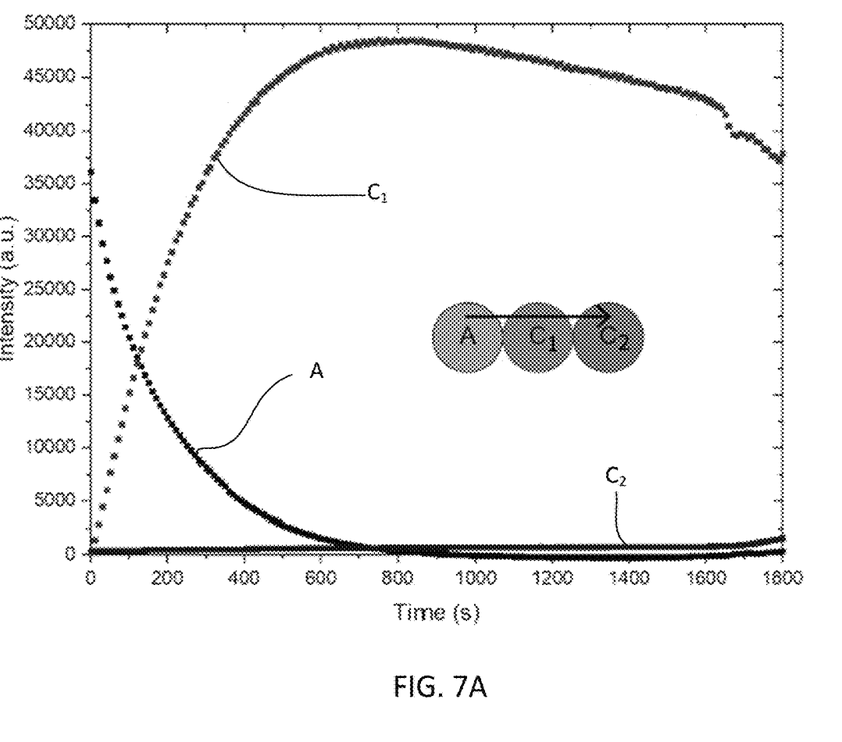
FIGS. 7A-7E are graphs of the change in fluorescence intensity over time for various embodiments of DIB networks.
Figure 7B:
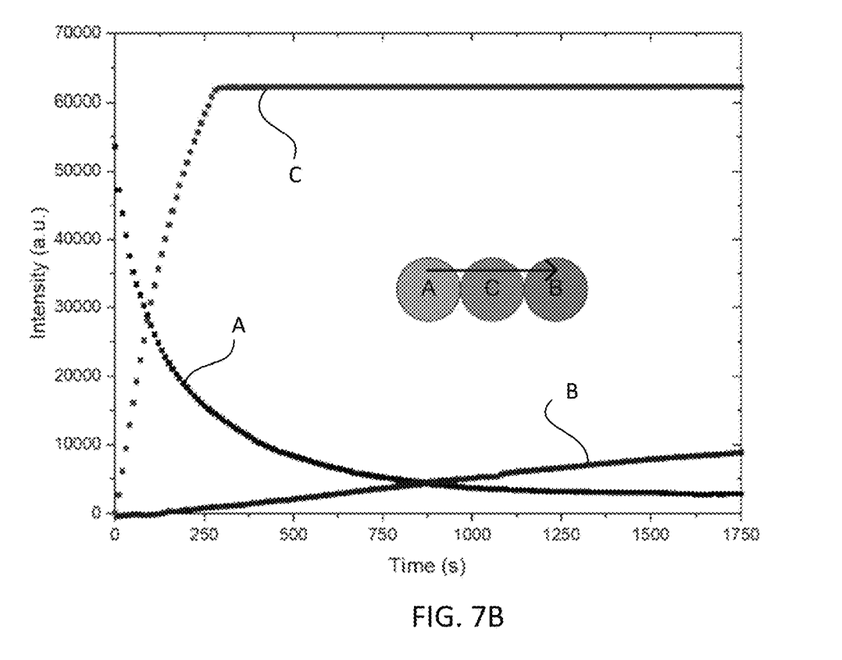
Figure 7C:
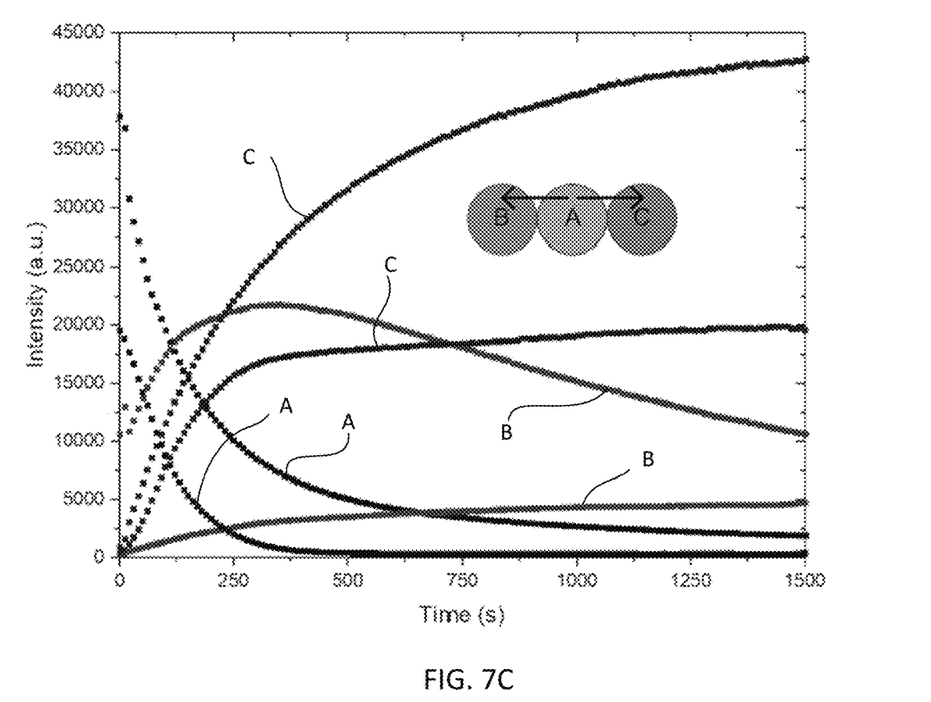
Figure 7D:
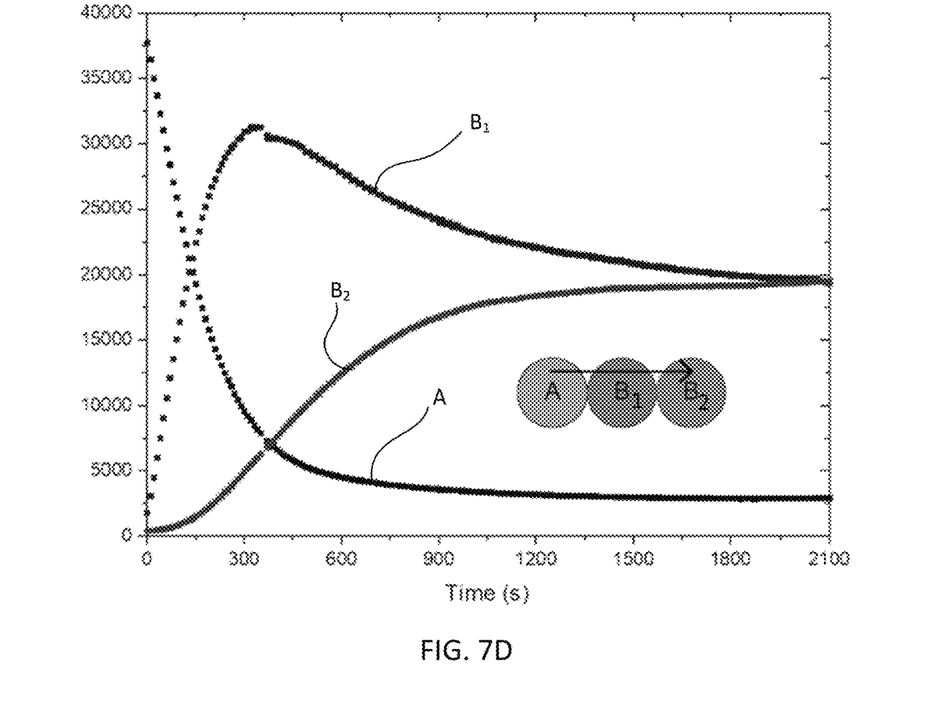
Figure 7E:
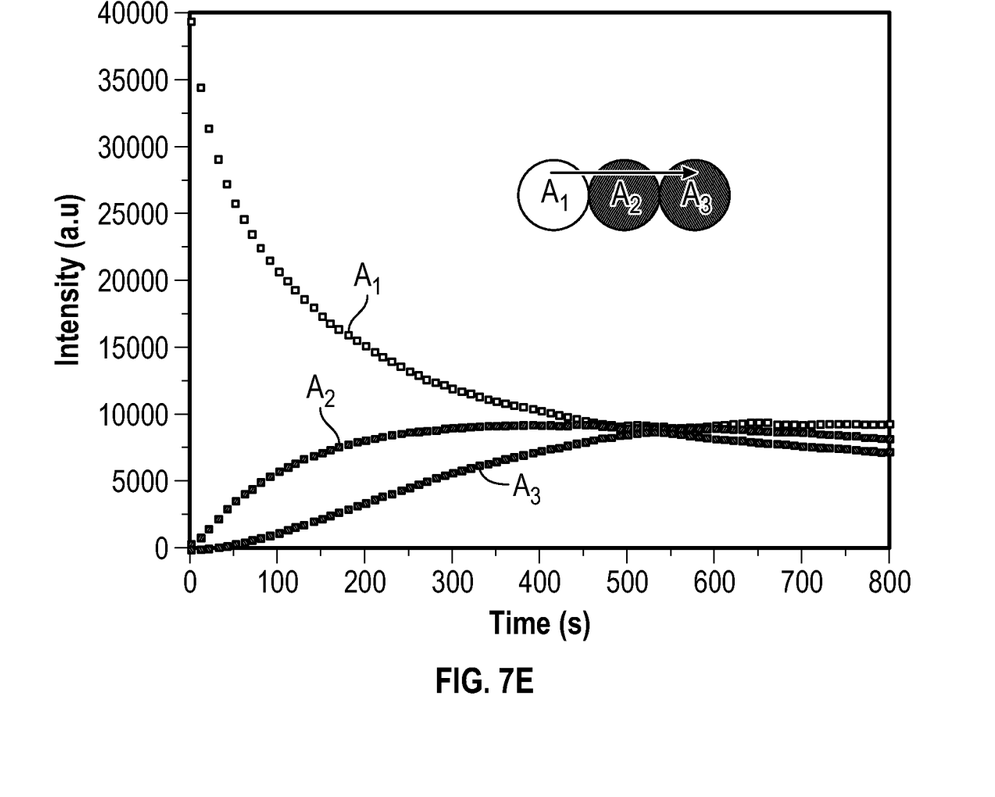

Direct comparison in intensity between the compartments is complicated by matrix differences since the composition of the droplets is customized using different buffering agents and salts. The experimentally determined Papp was compared against control experiments to assess the matrix effect. FIGS. 7A-7E are graphs of intensity over time for the control experiments described below. For example, the internal compositions of the droplets were varied such that different diffusion pathways could be tried. For example, if the intestinal space is represented as "A," the enterocyte as "B," and the blood as "C," the following combinations were experimentally assessed with the fluorophore dosed in droplet A: $A_1A_2A_3$ (FIG. 7E), BAC (FIG. 7C), $AB_1B_2$ (FIG. 7D), $AC_1C_2$(FIG. 7A), and ACB (FIG. 7B). As expected, complete fluorophore equilibration was observed when all three compartments were tuned to mimic the pH and ionic composition of the enterocyte ($A_1A_2A_3$). Likewise, when triplets of the composition BAC were formed, rapid equivalent diffusion out of droplet A into droplets B and C was observed, and in the case of $AB_1B_2$ triplets, rapid diffusion into droplet $B_1$ was followed by equilibration between both B droplets. The behavior of ACB triplets closely followed that of ABC triplets. However, when $AC_1C_2$ triplets were formed, rapid diffusion into $C_1$ occurred, and the fluorophore did not continue into the second C droplet, $C_2$. In all cases where pH 7.4 droplets were tested with pH 6.5 droplets, fluorescein demonstrated a clear preference for pH 7.4 compartments. Fluorescein has a pKa of 6.43, so a smaller fraction of molecules exist in the more lipid-soluble monoionic form at pH 7.4 and a larger fraction exist in the less lipid-soluble dianionic form at pH 6.5. This effectively allows fluorescein to easily diffuse into the artificial cell membrane from the intestinal space, but to diffuse back at a far reduced rate. This ties rate of diffusion to lipophilicity in the same way as PAMPA.

Figure 9:
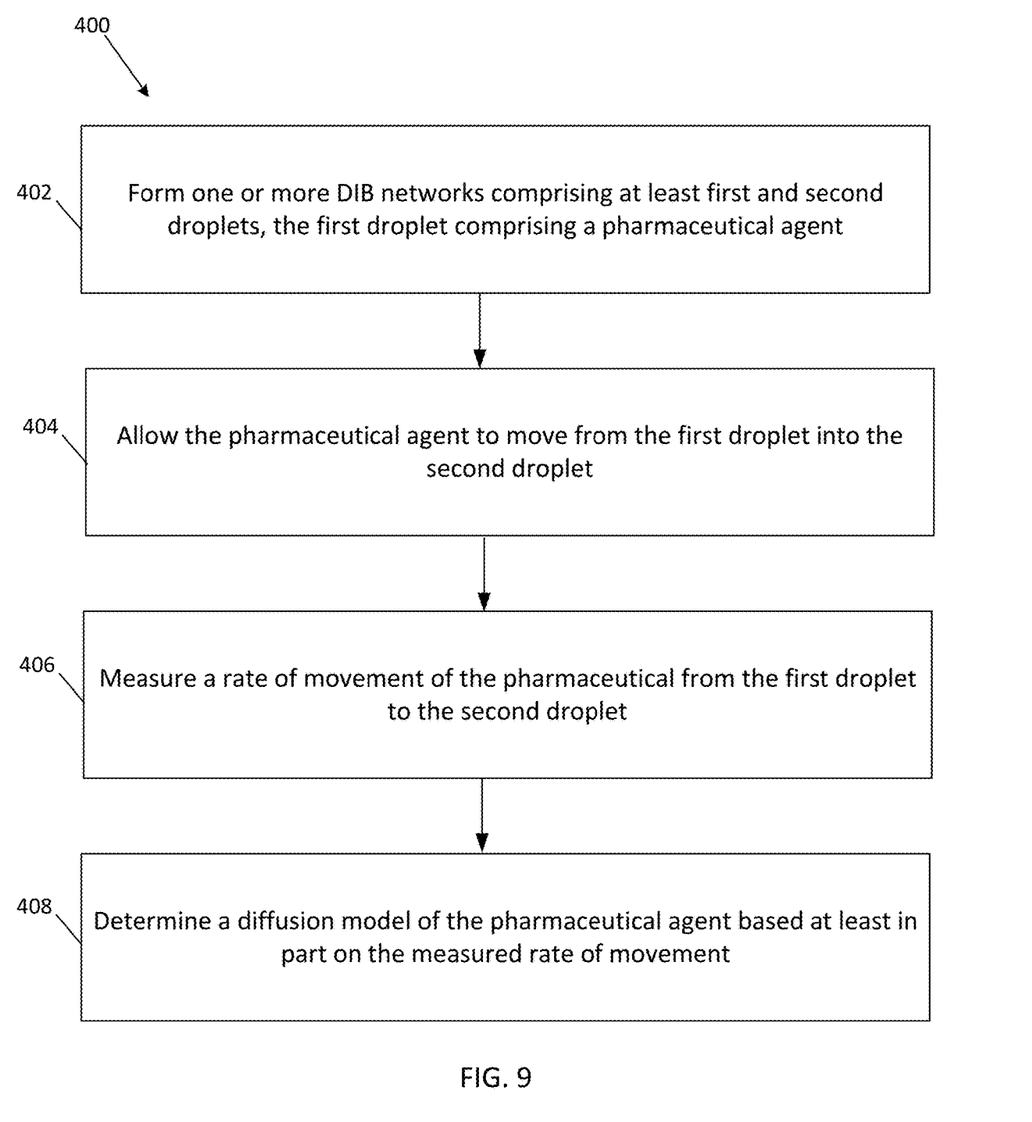
FIG. 9 is a process flow diagram of a representative method for determining a diffusion model of a pharmaceutical agent.

With reference to FIG. 9, a representative method of determining a diffusion model for a pharmaceutical agent can proceed as follows. At 402, one or more DIB networks can be formed comprising at least first and second droplets, the first droplet containing a pharmaceutical agent. At 404, the pharmaceutical agent can move or diffuse from the first droplet into the second droplet. At 406, the rate of movement of the pharmaceutical agent from the first droplet to the second droplet can be measured. At 408, a diffusion model of the pharmaceutical agent can be determined based at least in part on the measured rate of movement of the pharmaceutical agent.

EXAMPLE 3

An exemplary method of quantifying the performance of the microfluidic devices described herein can proceed as follows. Squalene was pumped into the non-miscible fluid inlet (e.g., non-miscible fluid inlet 120 of microfluidic device 100) and DPhPC in buffer was pumped into each of the three aqueous inlets (e.g., aqueous inlets 118) using a pressure pump in constant pressure mode. Assessment of the DIB network formed via the microfluidic device was performed using DPhPC to allow for comparison with other known DIB forming methodologies.

After letting the flow equilibrate, the high-speed camera was centered on the main chamber, and 60 seconds of footage were captured for each replicate. The number of DIB networks formed in each sequence was counted, as summarized in Table 2.

TABLE 2

Statistical data used to quantify device performance.

| n | Formation Rate | Oil Pressure | Aqueous Pressure |
|---|---|---|---|
| 34 | 0.57 Hz | 120 mbar | 113 mbar to 115 mbar |
| 32 | 0.53 Hz | 120 mbar | 113 mbar to 115 mbar |
| 26 | 0.43 Hz | 100 mbar | 90 mbar to 95 mbar |
| 18 | 0.30 Hz | 100 mbar | 90 mbar to 95 mbar |

The total number of droplets forming DB networks (e.g., tripartite networks comprising 3 droplets) was then determined as a percentage of the total number of droplets passing through the field of view. Two sets of two replicates each were carried out. For each replicate, a different microfluidic device was used. Statistical analysis indicated that DIB networks could be formed at a rate of 0.5±0.1 Hz and that 45±8% of droplets entering the rail section of the platform were able to form a DIB network.

EXAMPLE 4

An exemplary method of calibrating a heating platform, such as platform 300 described previously, can proceed as follows. The heating platform was calibrated using an ice water bath to determine whether the surface thermocouple was in good working condition. This was done by submerging the thermocouple probe in ice water and leaving it for 10 minutes to stabilize. After 10 minutes the measured value of the ice water on the controller was 0° C. for the surface thermocouple. Since the heating foils do not cover the entire surface of the base, the platform was also heated to 37° C. and 50° C. and observed with a thermal camera (FLIR) to determine the temperature variability on the surface of the heating platform.

The heating period of the base was determined by programming the base to heat and log the temperature readings over the course of 30 minutes at 5 second intervals. The base was set to heat up to 30° C., 37° C. and 50° C. The elapsed time before the readings stabilized (deviation of +/−0.1° C.) was 900 seconds, or approximately 15 minutes of heating.

EXAMPLE 5

An exemplary method of preparing lipid solutions used to form droplets in a DIB network proceeded as follows. To prepare the lipid solutions, chloroform was removed from the lipid stock solutions by placing the lipid stock in a 10 mL glass roundbottom flask, and rotating the flask under a stream of nitrogen gas to create a thin film. The flask was then placed in a desiccator under vacuum for 1 hour to remove residual solvent.

For polar brain lipid extract (porcine) solutions, 1 mL aqueous buffer (10 mM HEPES, 140 mM KCl, pH 7.59) was added to the flask, which was then vortexed to resuspend the lipids. After freezing and thawing 5 times using liquid nitrogen and warm water, the lipids were extruded 21 times through a 0.1 m polycarbonate membrane (e.g., from Avanti Polar Lipids) at room temperature. FIG. 10 illustrates an exemplary polar brain lipid extract (porcine) solution formed into a plurality of DIBs.

Figure 11:
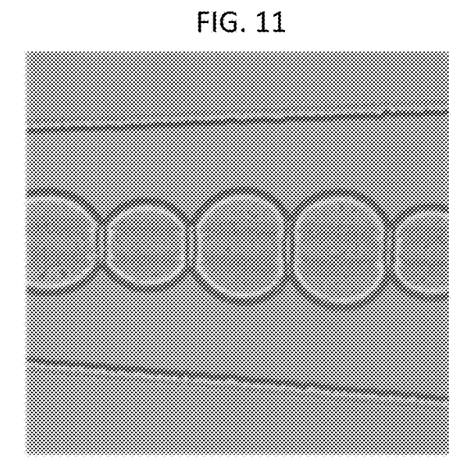

For intestine-mimetic lipid solutions including sphingomyelin and cholesterol, 1 mL of squalene was added to the flask, which was then vortexed for 30 seconds and stirred at 50° C. until the phospholipids dissolved. The final concentration was 4 mgmL$^{-1}$ PC, 4 mgmL$^{-1}$ PE, 1 mgmL$^{-1}$ PS, 1 mgmL$^{-1}$ PI, 5 mgmL$^{-1}$ cholesterol and 5 mgmL$^{-1}$ sphingomyelin. FIG. 11 illustrates an exemplary intestine-mimetic lipid solution formed into a plurality of DIBs.

Figure 12:
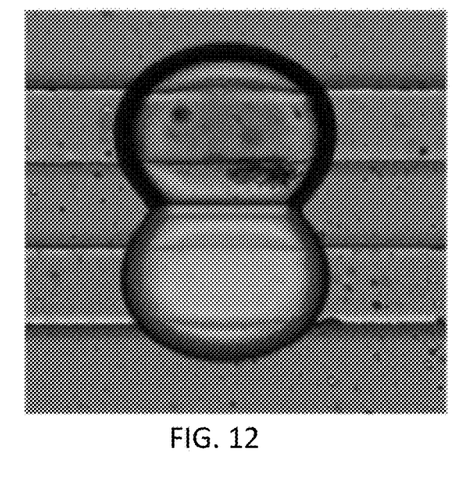

Referring to FIG. 12, for total brain lipid extract (porcine) solutions, 1 mL of squalene was added to the flask, which was then vortexed for 30 seconds and stirred at 50° C. until the phospholipids dissolved.

Figure 13:
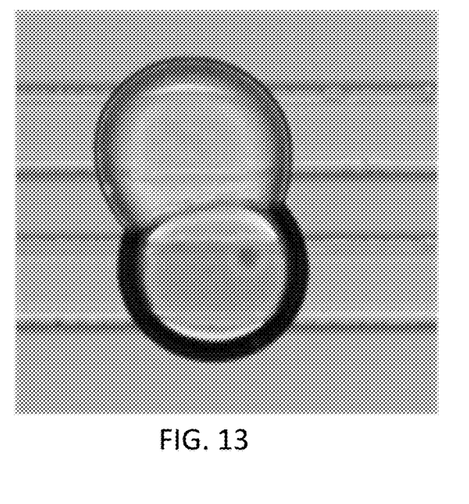

Referring to FIG. 13, when the pharmaceutical agent was doxorubicin, 1 mM doxorubicin was added to the buffer, and a mixture of the lipids PC, PE, sphingomyelin and cholesterol were dissolved in squalene at a molar equivalent to 5 mgmL$^{-1}$ of DPhPC.

Figure 14:
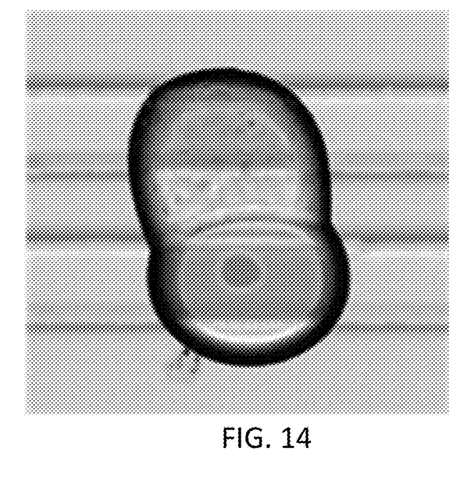

Referring to FIG. 14, for asymmetric bilayer formation, a mixture of the lipids PC, PE, sphingomyelin and cholesterol were dissolved in squalene at differing ratios, with final concentrations being a molar equivalent to 5 mgmL$^{-1}$ of DPhPC.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing material quantities, angles, pressures, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

The term "subject" as used herein refers to a human or a non-human animal.

In view of the many possible embodiments to which the principles of the disclosure may be applied, it should be recognized that the illustrated embodiments are only preferred examples and should not be taken as limiting the scope of the disclosure. Rather, the scope is defined by the following claims. We therefore claim all that comes within the scope and spirit of these claims.

The invention claimed is:

1. A composition, comprising:
   at least two adjacent droplets with at least one phospholipid bilayer between them;
   wherein the at least one phospholipid bilayer comprises phospholipids associated with mammalian cells; and
   wherein at least one droplet is configured to mimic an entry point of at least one pharmaceutical agent into a subject.

2. The composition of claim 1, wherein the phospholipid bilayer comprises L-α-phosphatidylcholine (PC) and L-α-phosphatidylethanolamine (PE).

3. The composition of claim 1, wherein the phospholipid bilayer comprises cholesterol, sphingomyelin, phosphatidylserine (PS), phosphatidylinositol (PI), and/or lipid extracts.

4. The composition of claim 1, wherein the phospholipid bilayer comprises one or more other molecules associated with mammalian cell membranes such as carbohydrates, glycolipids and/or glycoproteins.

5. The composition of claim 1, wherein the phospholipid bilayer comprises one or more membrane proteins.

6. The composition of claim 1, wherein the phospholipid bilayer can comprise two phospholipid monolayers, and wherein the phospholipid monolayers have different compositions such that they form an asymmetric phospholipid bilayer.

7. The composition of claim 1, wherein there are one to eight intermediate barriers between the entry point and an area of pharmaceutical action.

8. The composition of claim 1, wherein the at least two adjacent droplets comprise first, second, and third droplets and wherein the first droplet is configured to mimic an intestinal space of a subject, the second droplet is configured to mimic an intestinal cell cytosol of the subject, and the third droplet is configured to mimic the subject's blood.

9. The composition of claim 1, wherein the at least one pharmaceutical agent enters or exits the droplet from at least one non-miscible fluid surrounding at least a first droplet.

10. The composition of claim 9, wherein lipids are inserted into a fluid disposed within at least one droplet and/or the non-miscible fluid.

11. The composition of claim 1, wherein the DIB networks are created at different temperatures.

12. A microfluidic device for creating the composition of claim 1, comprising:
   a plurality of channels defined in a substrate, each channel comprising a respective channel inlet, a respective channel outlet, and one or more respective non-miscible fluid inlets fluidly coupled to the channel inlet;
   a plurality of rails defined in the substrate, each rail comprising a rail inlet, wherein each channel outlet is coupled to a respective rail inlet;
   wherein one or more fluids introduced via the channel inlets can form at least a first, and second droplet, respectively; and
   wherein the plurality of rails comprises at least first, and second rails configured to taper toward one another such that the at least first, and second droplets disposed on the rails contact one or more adjacent droplets to form at least a 2-part droplet interface bilayer (DIB) network.

13. The microfluidic device of claim 12, wherein at least a portion of each rail is parallel to one or more adjacent rails such that the DIB networks are formed in parallel from droplets disposed on adjacent rails.

14. The microfluidic device of claim 12, wherein the substrate comprises a first layer and a second layer, wherein the plurality of channels are disposed in the first layer, and wherein the plurality of rails are disposed in the second layer.

15. The microfluidic device of claim 12, wherein at least one channel comprises a meander such that the plurality of channels have equal lengths.

16. The microfluidic device of claim 12, wherein at least one non-miscible fluid inlet comprises a meander such that all non-miscible fluid inlets have equal lengths.

17. The microfluidic device of claim 12, wherein at least one channel comprises a meander sized to allow a droplet disposed within the at least one channel to equilibrate.

18. A method, comprising:
    forming one or more DIB networks comprising at least first and second droplets having at least one phospholipid bilayer between them, the at least one phospholipid bilayer comprising phospholipids associated with mammalian cells, the first droplet being configured to mimic an entry point of at least one pharmaceutical agent into a subject and comprising at least one pharmaceutical agent;
    allowing the at least one pharmaceutical agent to move from the first droplet into the second droplet;
    measuring a rate of movement or no movement of the at least one pharmaceutical agent from the first droplet to the second droplet; and
    determining a diffusion or transport model of the at least one pharmaceutical agent based at least in part on the rate of movement;
    wherein the first and second droplet have different compositions and/or concentrations of pharmaceutical agent from one another.

19. The method of claim 18, wherein the DIB network further comprises a third droplet, wherein the method further comprises allowing the at least one pharmaceutical agent to move from the second droplet into the third droplet or vice versa, and wherein the third droplet is disposed between the first and second droplets, or wherein the first droplet is disposed between the second and third droplets, or wherein the second droplet is disposed between the first and third droplets.

20. The method of claim 18, wherein measuring a rate of movement comprises measuring a rate of movement of the at least one pharmaceutical agent from the first droplet to a selected droplet of the second and third droplets or vice versa.

21. The method of claim 18, wherein there are one to eight intermediate barriers between the entry point and an area of pharmaceutical action.

22. The method of claim 18, wherein measuring a rate of movement comprises measuring a first rate of movement from a space external to a droplet to an internal space within the droplet or vice versa.

23. The method of claim 18, wherein forming the one or more DIB networks comprises:
    disposing the first and second droplets into first and second channels, respectively;
    flowing a non-miscible fluid through first and second channels to carry the droplets into first and second rails;
    wherein the first and second rails are configured to guide the droplets together to form a DIB network.

* * * * *